United States Patent
Shah et al.

(10) Patent No.: US 9,888,756 B2
(45) Date of Patent: Feb. 13, 2018

(54) ITEM AND LUGGAGE LOSS PREVENTION SYSTEM

(71) Applicant: Nolo Holdings LLC, Boise, ID (US)

(72) Inventors: Faisal Shah, Boise, ID (US); Terry Gafron, Boise, ID (US)

(73) Assignee: Nolo Holdings LLC, Boise, ID (US)

( * ) Notice: Subject to any disclaimer, the term of this patent is extended or adjusted under 35 U.S.C. 154(b) by 250 days.

(21) Appl. No.: 14/605,590

(22) Filed: Jan. 26, 2015

(65) Prior Publication Data

US 2015/0237980 A1 Aug. 27, 2015

Related U.S. Application Data

(60) Provisional application No. 61/943,765, filed on Feb. 24, 2014, provisional application No. 62/046,690, filed on Sep. 5, 2014.

(51) Int. Cl.

| | |
|---|---|
| *A45C 13/18* | (2006.01) |
| *G01G 19/52* | (2006.01) |
| *G01G 19/58* | (2006.01) |
| *G01G 23/365* | (2006.01) |
| *A45C 13/24* | (2006.01) |
| *G08B 21/24* | (2006.01) |
| *A61B 5/11* | (2006.01) |
| *G08B 21/22* | (2006.01) |

(52) U.S. Cl.
CPC ............. *A45C 13/18* (2013.01); *A45C 13/24* (2013.01); *A61B 5/1115* (2013.01); *G01G 19/52* (2013.01); *G01G 19/58* (2013.01); *G01G 23/365* (2013.01); *G08B 21/24* (2013.01); *A61B 2503/04* (2013.01); *A61B 2503/06* (2013.01); *G08B 21/22* (2013.01)

(58) Field of Classification Search
CPC ..... A45C 13/18; A45C 13/24; A61B 2503/04; A61B 2503/06; A61B 5/1115; G01G 19/52; G01G 19/58; G01G 23/365; G08B 21/22; G08B 21/24

See application file for complete search history.

(56) References Cited

U.S. PATENT DOCUMENTS

| | | | |
|---|---|---|---|
| 5,148,150 A * | 9/1992 | White ................ | G08B 13/1436 200/61.52 |
| 7,084,357 B2 * | 8/2006 | Roberts .................. | A45C 15/00 177/131 |

(Continued)

*Primary Examiner* — Nay Tun

(74) *Attorney, Agent, or Firm* — Swanson & Bratschun, L.L.C.

(57) ABSTRACT

Novel tools and techniques are provided for implementing item or luggage loss prevention, which, in some cases, is based on weight measurement. In some embodiments, a device with a processor can be placed under a bag's handle, within an interior compartment of the bag, below or in the feet or wheels of the bag, and/or the like. The device can allow a user to lock in a weight of the bag. If any item is subsequently removed from (and not returned to) the bag, the device will notify the user, using one or more of audio notification, visual notification, and/or mobile device notification (e.g., via e-mail, text message, SMS, MMS, chat message, and/or the like) that the weight of the bag has changed. In some cases, location detection devices may be implemented to allow the user to backtrack where the missing item might have been left behind.

26 Claims, 7 Drawing Sheets

(56) References Cited

U.S. PATENT DOCUMENTS

| | | | | |
|---|---|---|---|---|
| 7,535,358 B2 * | 5/2009 | Crider | ................... | G06Q 10/08 340/545.6 |
| 7,889,078 B2 * | 2/2011 | Hoyden | ............. | G08B 13/1427 340/545.4 |
| 8,212,665 B2 | 7/2012 | Schoenberg et al. | | |
| 8,477,024 B2 | 7/2013 | Schoenberg et al. | | |
| 8,901,442 B1 * | 12/2014 | Dilone | ................... | A45C 13/18 177/127 |
| 2005/0217903 A1 * | 10/2005 | Roberts | ................. | A45C 15/00 177/245 |
| 2006/0086541 A1 * | 4/2006 | Khan | ..................... | A45C 13/24 177/45 |
| 2006/0266563 A1 * | 11/2006 | Kaplan | ................. | G01G 19/58 177/245 |
| 2007/0222587 A1 * | 9/2007 | Crider | ................... | G06Q 10/08 340/539.13 |
| 2009/0146808 A1 * | 6/2009 | Hoyden | ............. | G08B 13/1427 340/568.1 |
| 2012/0186926 A1 * | 7/2012 | Sheikh | .................... | A45C 5/03 190/115 |
| 2013/0175099 A1 * | 7/2013 | Tazawa | ................. | G01G 19/40 177/25.13 |

\* cited by examiner

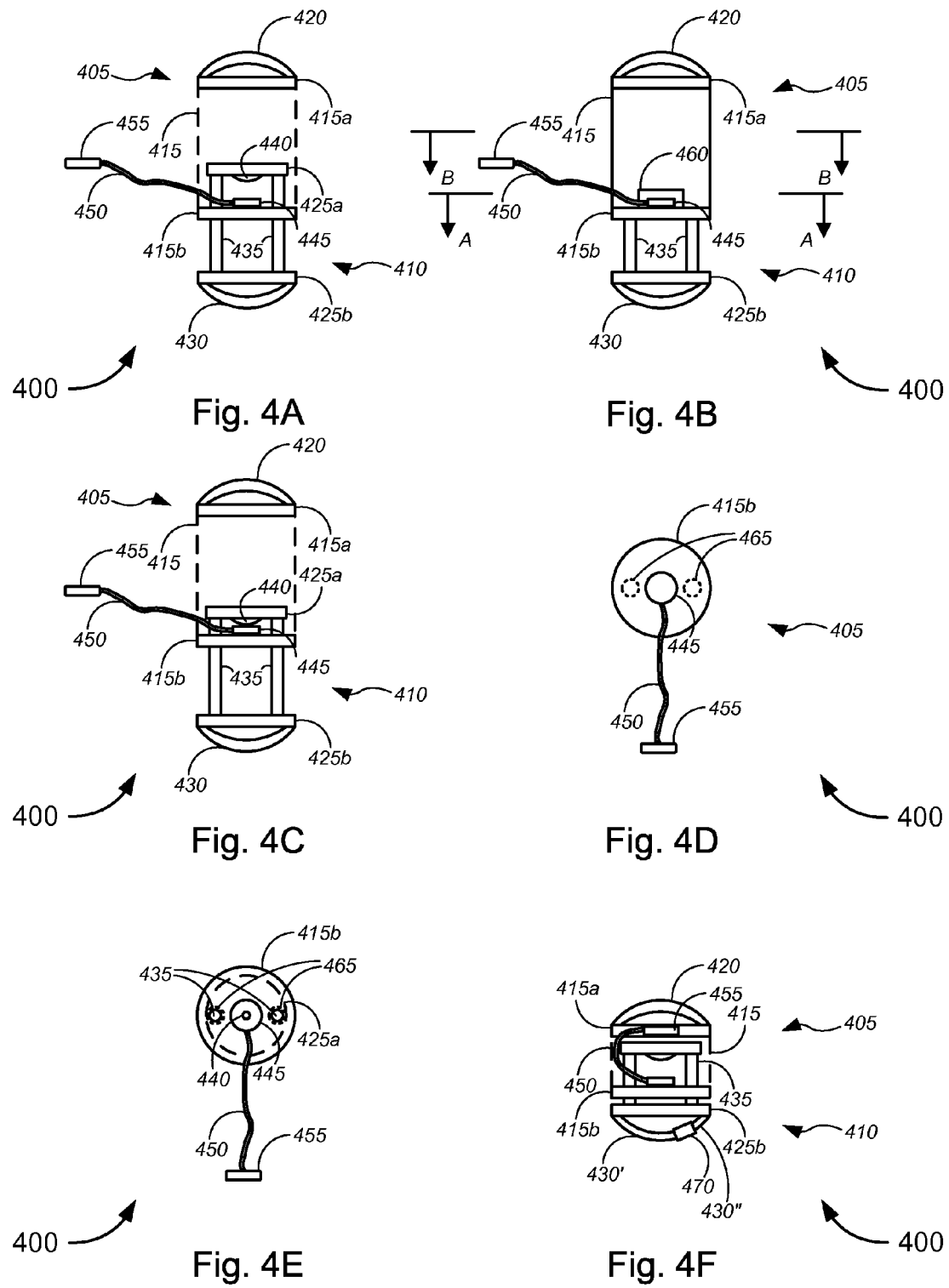

500

ITEM AND LUGGAGE LOSS PREVENTION SYSTEM

CROSS-REFERENCE TO RELATED APPLICATIONS

This application claims priority to U.S. Patent Application Ser. No. 61/943,765 (the "'765 application"), filed Feb. 24, 2014 by Faisal Shah and titled "Item and Luggage Loss Prevention System" and U.S. Patent Application Ser. No. 62/046,690 (the "'690 application"), filed Sep. 5, 2014 by Faisal Shah et al. and titled "Item and Luggage Loss Prevention System."

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to a device, system, and method for preventing loss of items or luggage, and, more particularly, to a device, system, and method for preventing loss of items or luggage based on weight measurements.

BACKGROUND

Airports around the world have an epidemic. People are losing valuable items every time they go through the security checkpoint(s) at airports. This is because one of the requirements of airport security is that travelers must remove their laptops from their bags. Another requirement is that travelers remove phones and other metallic objects from their persons before passing through the scanners. As a consequence, there is a natural tendency for travelers to walk away without collecting their items (including, without limitation, laptops, smart phones, tablet computers, cellular phones, media players, and/or the like). Approximately 1.7 million people travel through U.S. airports each day. Items are lost everywhere in the airports, including, but not limited to, on planes, in terminal gates, in lounges, and/or the like. It is estimated that over 16,000 laptops are left at U.S. airports each year. The laptop loss alone is estimated to be around $700 million.

Travelers' items left in airports also put a significant strain on the already over-worked security personnel such as Transportation Security Administration ("TSA") personnel in the U.S. It requires that such personnel retain and manage custody of such lost items. Currently, such lost items are collected by TSA agents and held for 30 days. After the 30-day period expires, the hard drives and/or memory are removed and the items are put on auction. All the information in the computing devices is subsequently destroyed. This process requires man-hours for collecting the lost items, tracking how long the lost items have been held, removing data storage drives, destroying information stored in the devices, and auctioning the items.

Third party non-governmental Lost and Found web sites have been established in an effort to help people recover their lost items. It is unclear, however, how successful these sites are. But, for such sites to be useful, the travelers would have to know about a particular site in order to be able to post that they have lost something at a particular airport. It would also require that the person who has possession of the lost item(s) know about the site so that they can contact the person that lost such item(s). In general, such web sites only serve to work on the recovery of lost items, but cannot help to prevent loss of the items in the first place.

In terms of the use of weight measurement of luggage, existing travel scales provide weighing functionality, but such devices are incapable of alerting a traveler of a change in weight (such as when an item has not been put back in the luggage, or the like).

Hence, there is a need for more robust and scalable solutions for preventing item and luggage loss.

BRIEF SUMMARY

Various embodiments provide techniques for implementing item or luggage loss prevention, which, in some cases, is based on weight measurements.

According to some embodiments, a device containing a processor might be configured to be placed under a bag's handle. The device might contain a small display (including, without limitation, a liquid crystal display ("LCD"), a light emitting diode ("LED") display, an organic LED ("oLED") display, and/or the like) and a processor. The device might allow the user to lock in a weight of a bag. If any item is then removed from (and not returned to) the bag, the device might notify the user (e.g., using audio notification (e.g., recorded voice notification, beeps, and/or the like), visual notification (e.g., blinking lights, flashing icons, written messages, and/or the like), and/or mobile device notification (e.g., e-mail notification, text message notification, small message service ("SMS") notification, multi-media messaging service ("MMS") notification, chat message notification, and/or the like) that the weight of the bag has changed (from the locked-in weight). In some embodiments, the device might comprise an LCD display for the weight and notification, an on or off button, and one or more button(s) to store/lock-in a weight (or to change the lock-in weight) and to release or delete any locked-in or stored weights.

The tools provided by various embodiments include, without limitation, methods, systems, and/or software products. Merely by way of example, a method might comprise one or more procedures, any or all of which might be executed by a computer system. Correspondingly, an embodiment might provide a computer system configured with instructions to perform one or more procedures in accordance with methods provided by various other embodiments. Similarly, a computer program might comprise a set of instructions that are executable by a computer system, or by a processor located in the computer system, to perform such operations. In many cases, such software programs are encoded on physical, tangible, and/or non-transitory computer readable media. Such computer readable media might include, to name but a few examples, optical media, magnetic media, and the like.

In an aspect, a method might comprise receiving, with a device, a first user input from a user to lock-in a first weight of a bag, measuring, with the device, the first weight of the bag, in response to receiving the first user input, and storing, with the device and in a local data storage device, the measured first weight of the bag, prior to the user removing one or more items from the bag. The method might further comprise measuring, with the device, a second weight of the bag, for example, in response to second user input, in response to determining that the bag is being moved, etc. The method, then, might include determining, with the device, whether the second weight of the bag matches the stored first weight of the bag. The method might also comprise, based on a determination that the second weight does not match the first weight, notifying, with the device, the user.

According to some embodiments, measuring each of the first weight and the second weight might comprise measuring using a weight measurement device comprising a contact surface and a contact sensor. The weight measurement device might have a structure that causes the contact surface to be brought into contact with the contact sensor when a first portion of the weight measurement device is lifted with respect to a second portion of the weight measurement device, which is coupled to the bag. In some cases, the contact sensor might comprise at least one of a flex sensor, a piezoelectric-based sensor, a compression-based sensor, and/or a spring-based sensor.

In some embodiments, the device might be attached to the bag. The bag, according to some embodiments, might comprise one or more of a purse, a handbag, a tote, a briefcase, a satchel, laptop bag, travel bag, or carry-on luggage. In some cases, the device might be attached to one or more handles of the bag. The device, in some instances, might be placed in an interior compartment of the bag. In some embodiments, the device might be placed at a bottom portion of the interior compartment of the bag (ideally, below the one or more items when the one or more items are placed in the bag). According to some embodiments, the device might be placed below one or more feet of the bag. In some cases, the device might be affixed to a position between the bag and each of one or more wheel casters of the bag. In alternative cases, the device might be positioned within one or more wheel casters of the bag.

In some aspects, measuring each of the first weight and the second weight might comprise measuring using a weight measurement device comprising a load cell selected from a group consisting of a strain gauge load cell, a piezoelectric load cell, a capacitive load cell, a compression load cell, a compression/tension load cell, an S-beam load cell, a bending beam load cell, a platform load cell, a single point load cell, a canister load cell, and a low profile load cell. Determining that the bag is being moved might, in some embodiments, comprise determining, with the device, that the load cell of the weight measurement device is being actuated (which might indicate that the bag is being lifted).

In some cases, determining that the second weight does not match the first weight might comprise determining that the second weight is less than the first weight. In some instances, determining that the second weight does not match the first weight might comprise determining that the second weight is greater than the first weight. In either case, notifying the user might comprise reminding the user to check that the one or more items that were removed from the bag have been returned to the bag.

According to some embodiments, the method might further comprise determining, with a location detection device of the device, a first location of the device when measuring the first weight of the bag, and storing, with the device, the first location in the local data storage device. Notifying the user might comprise sending a message containing the first location. In some embodiments, the method might also comprise determining, with the location detection device of the device, a second location of the device when measuring the second weight of the bag, and storing, with the device, the second location in the local data storage device. Notifying the user might comprise sending a message containing each location where a weight of the bag was measured (this might allow the user to retrace where a lost item might be located, i.e., by retracing where the item might have been removed from the bag). In embodiments in which the device comprises a location detection device, determining that the bag is being moved might comprise determining, with the location detection device, that a present location of the device is different from the first location of the device.

In some embodiments, the method might further comprise determining, with the device, which of one or more items is missing from the bag based on a difference between the first weight and the second weight. This might include pre-storing a plurality of weights of the bag, with and without each of the one or more items. Notifying the user might further comprise indicating which of the one or more items might be missing based on the determination.

Merely by way of example, in some cases, notifying the user might comprise one or more of playing a recorded voice notification, emitting one or more audio tones, displaying one or more light sequences, displaying one or more icons, displaying a written message, sending an e-mail notification, sending a text message notification, sending a small message service ("SMS") notification, sending a multi-media messaging service ("MMS") notification, or sending a chat message notification.

In another aspect, an apparatus might comprise at least one processor, a weight measurement device, a user interface device, and a computer readable storage medium in communication with the at least one processor. The computer readable storage medium might have stored thereon computer software. The computer software might comprise a set of instructions that, when executed by the at least one processor, causes the apparatus to perform one or more operations. The set of instructions might comprise instructions to receive a first user input from a user to lock-in a first weight of a bag, instructions to measure the first weight of the bag, in response to receiving the first user input, and instructions to store the measured first weight of the bag in the computer readable storage medium, prior to the user removing one or more items from the bag. The set of instructions might further comprise instructions to determine that the bag is being moved, instructions to measure a second weight of the bag, and instructions to determine whether the second weight of the bag matches the stored first weight of the bag. The set of instructions might also comprise instructions to, based on a determination that the second weight does not match the first weight, notify the user.

According to some embodiments, the apparatus might further comprise a location detection device (including, without limitation, a global positioning system ("GPS"), position triangulation transceivers, and/or the like). In some cases, the apparatus might further comprise a network interface device (including, but not limited to, Bluetooth™ device, an 802.11 device, a WiFi device, a WiMax device, a WWAN device, cellular communication devices, and/or the like). The user interface device, in some embodiments, might comprise one or more of one or more display devices, one or more audio speakers, one or more touchscreen display devices, one or more buttons, one or more switches, or one or more light emitting devices.

In yet another aspect, a method might comprise determining, with a device, that a weight of a bag has changed, and in response to such determination, notifying, with the device, that one or more items may be missing from the bag based on the determined change in weight.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 4A-4F are general schematic diagrams illustrating various views and configurations of an apparatus for implementing item or luggage loss prevention, in accordance with various embodiments.

DETAILED DESCRIPTION OF CERTAIN EMBODIMENTS

Figure 1:
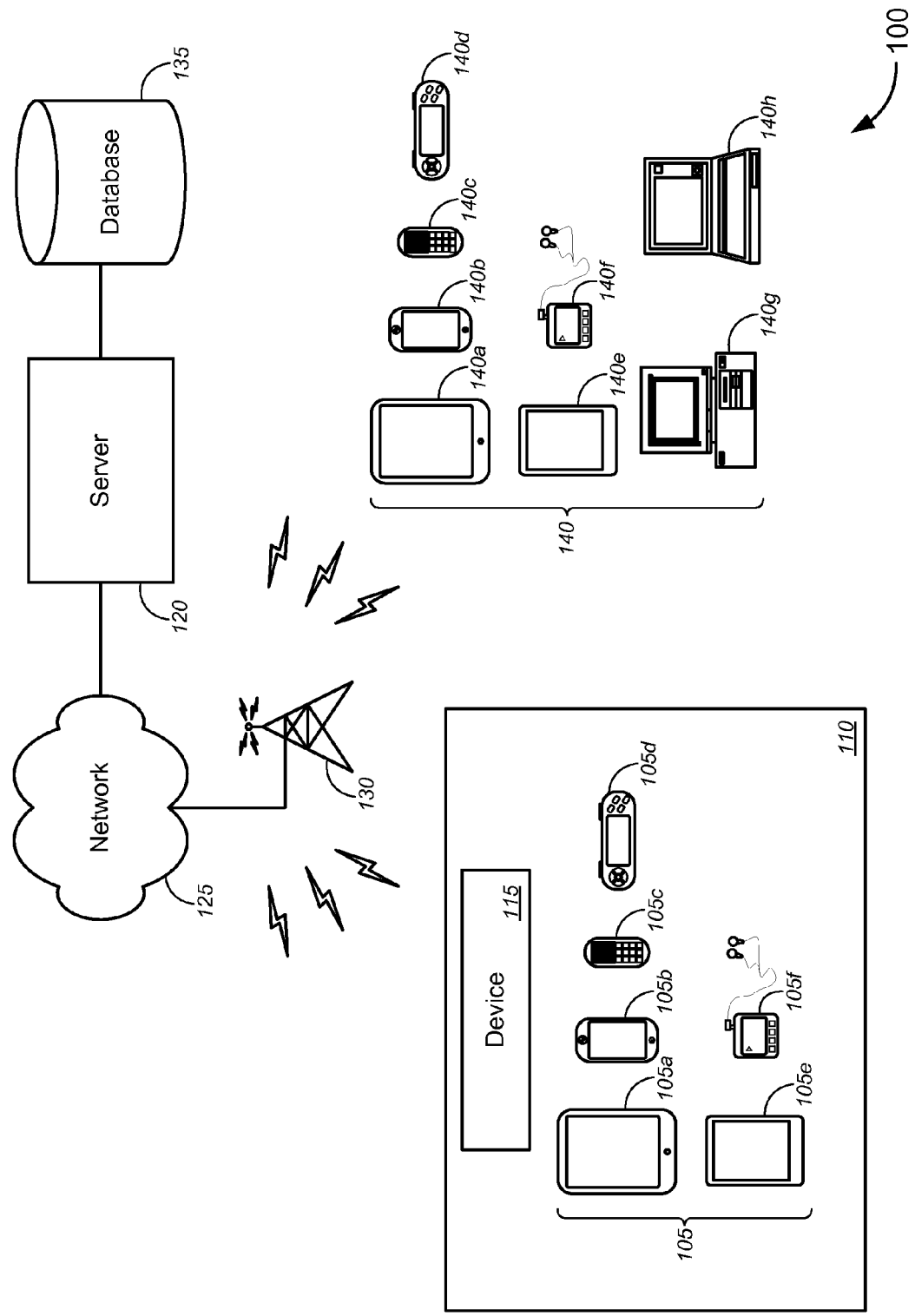
FIG. 1 is a general schematic diagram illustrating a system for implementing item or luggage loss prevention, in accordance with various embodiments.

While various aspects and features of certain embodiments have been summarized above, the following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments provide techniques for implementing item or luggage loss prevention, which, in some cases, is based on weight measurements.

According to some embodiments, a device containing a processor might be configured to be placed under a bag's handle. The device might contain a small display (including, without limitation, a liquid crystal display ("LCD"), a light emitting diode ("LED") display, an organic LED ("oLED") display, and/or the like) and a processor. The device might allow the user to lock in a weight of a bag. If any item is then removed from (and not returned to) the bag, the device might notify the user (e.g., using audio notification (e.g., recorded voice notification, audio tones, beeps, and/or the like), visual notification (e.g., blinking lights, flashing icons, written messages, and/or the like), and/or mobile device notification (e.g., e-mail notification, text message notification, small message service ("SMS") notification, multimedia messaging service ("MMS") notification, chat message notification, and/or the like) that the weight of the bag has changed (from the locked-in weight). In some embodiments, the device might comprise an LCD display for the weight and notification, an on or off button, and one or more button(s) to store/lock-in a weight (or to change the lock-in weight) and to release or delete any locked-in or stored weights.

In operation, prior to purposefully removing an item(s) (including, without limitation, a laptop computer, a smart phone, a mobile phone, a portable gaming device, a portable media player, a tablet computer, an e-book reader, and/or the like) from a bag (including, but not limited to, a purse, a handbag, a tote, a briefcase, a satchel, laptop bag, travel bag, carry-on luggage, and/or the like), the user can lock-in a weight of the bag using the device described above. This is applicable, for example, during security check-in at an airport terminal, during a meal in a restaurant, during a meeting, during a typical workday at the office, during school hours, and/or the like. If the user starts to walk away without the item(s) being returned to the bag, the device will issue a notification, which may take one or more forms, including, without limitation, audio notifications (e.g., recorded voice notification, beeps, and/or the like), visual notifications (e.g., blinking lights, flashing icons, written messages, and/or the like), and/or mobile device notifications (e.g., e-mail notification, text message notification, SMS notification, MMS notification, chat message notification, and/or the like).

We now turn to the embodiments as illustrated by the drawings. FIGS. 1-7 illustrate some of the features of the method, system, and apparatus for implementing item or luggage loss prevention, as referred to above. The methods, systems, and apparatuses illustrated by FIGS. 1-7 refer to examples of different embodiments that include various components and steps, which can be considered alternatives or which can be used in conjunction with one another in the various embodiments. The description of the illustrated methods, systems, and apparatuses shown in FIGS. 1-7 is provided for purposes of illustration and should not be considered to limit the scope of the different embodiments.

With reference to the figures, FIG. 1 is a general schematic diagram illustrating a system 100 for implementing item or luggage loss prevention, in accordance with various embodiments. In FIG. 1, system 100 might comprise one or more user devices 105, a bag 110, and device 115. The one or more user devices 105 might comprise one or more tablet computers 105a, one or more smart phones 105b, one or more mobile phones 105c, or one or more portable gaming devices 105d, one or more e-book readers 105e, one or more media players 105f (such as an MP3 audio player, or the like), and/or the like. The bag 110 might include one of a purse, a handbag, a tote, a briefcase, a satchel, laptop bag, travel bag, carry-on luggage, and/or the like. Device 115 is an item or luggage loss prevention device as described in greater detail below with respect to FIGS. 2 and 3.

System 100 might further comprise server 120 communicatively coupled to the device 115 via network 125 (which might be an access network), and in some cases via one or more telecommunications relay systems 130. The one or more telecommunications relay systems 130 might include, without limitation, one or more wireless network interfaces (e.g., wireless modems, wireless access points, and the like), one or more towers, one or more satellites, and the like. System 100 might further comprise database 135 in communication with server 120.

In some embodiments, system 100 might further comprise a plurality of user devices 140, which might include, without limitation, one or more tablet computers 140a, one or more smart phones 140b, one or more mobile phones 140c, or one or more portable gaming devices 140d, one or more e-book readers 140e, one or more media players 140f (such as an MP3 audio player, or the like), one or more desktop computers 140g, one or more laptop computers 140h, and/or the like. In some cases, the one or more tablet computers 140a, one or more smart phones 140b, one or more mobile phones 140c, or one or more portable gaming devices 140d, one or more e-book readers 140e, one or more media players 140f might be the same as the one or more tablet computers 105a, one or more smart phones 105b, one or more mobile phones 105c, or one or more portable gaming devices 105d, one or more e-book readers 105e, one or more media players 105f.

In operation, device 115 might allow a user to lock-in a first weight of bag 110 containing the one or more user devices 105. When the user removes at least one of the one or more user devices 105 (e.g., during airport security check-in, during the work day, during a meal, during school, and/or the like), the first weight will have been stored in memory (either on the device 115 locally, or in database 135 via server 120 and network 125). When the user moves the bag, the device 115 might determine that the bag is being moved. In some instances, this might be accomplished by sensing, using a weight measurement device of device 115, that the bag is being lifted. Alternatively, or additionally, the device 115 might comprise a location detection device (e.g., a GPS device, a location triangulation transceiver, and/or the like), which might be used to determine a change in location of the device 115 and/or the bag 110.

Once it is determined that the bag 110 is being moved, the device 115 might measure a second weight of the bag 110, and might determine whether the second weight is different from the first weight. If so, the device 115 might notify the user that the weight of bag 110 has changed. Notification, in some cases, might take the form of audio notification, visual notification, and/or wireless notification. Audio notification might include, without limitation, recorded voice notification, audio tones, beeps, and/or the like). Visual notification might include, but is not limited to, blinking lights, flashing icons, written messages, and/or the like. Wireless notification might include, without limitation, e-mail notification, text message notification, small message service ("SMS") notification, multi-media messaging service ("MMS") notification, chat message notification, and/or the like. In the case of wireless notification, a network interface device of the device 115 might communicate with server 120 via network 125 (and, in some instances, via the one or more telecommunications relay systems 130). The server 120 might send the e-mail, text, SMS, MMS, and/or chat notifications via network 125 (and, in some instances, via the one or more telecommunications relay systems 130) to the one or more user devices 140. Alternatively, device 115 might directly send the e-mail, text, SMS, MMS, and/or chat notifications via network 125 (and, in some instances, via the one or more telecommunications relay systems 130) to the one or more user devices 140.

In some embodiments, the one or more user devices 140 might be associated with the user (or owner of bag 110), while in other cases, the one or more user devices 140 might be associated with a family member or friend (e.g., a travelling companion) of the user (or owner of bag 110). Such preferences for sending the notification can be set up by the user on the device 115 itself and/or at the server 120 (e.g., via a user interface (such as a web user interface, or an App interface, or the like)). In some cases, a spouse (or boyfriend or girlfriend), or a parent, of the owner of the bag 110 might set up the device 115 to notify him- or herself (and/or to notify the owner of the bag 110).

Figure 2A:
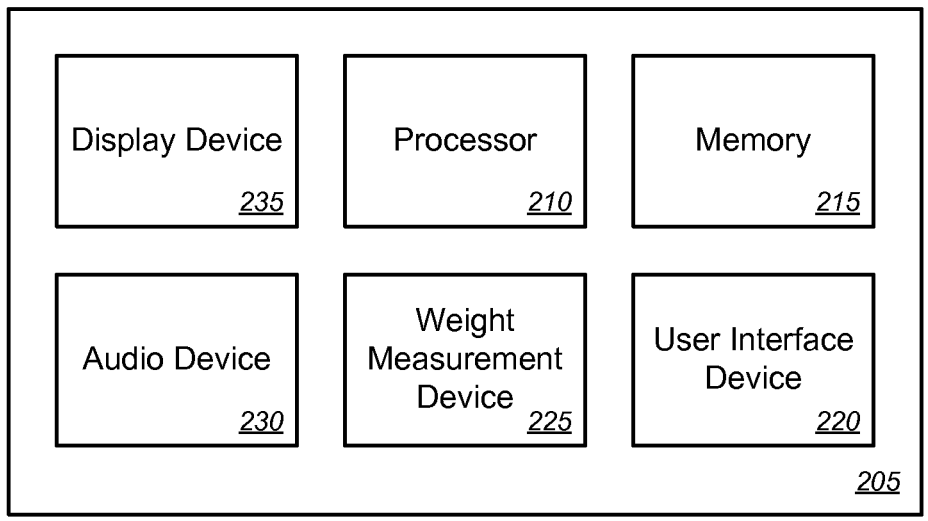
FIGS. 2A and 2B are general block diagrams illustrating various apparatuses for implementing item or luggage loss prevention, in accordance with various embodiments.
Figure 2B:
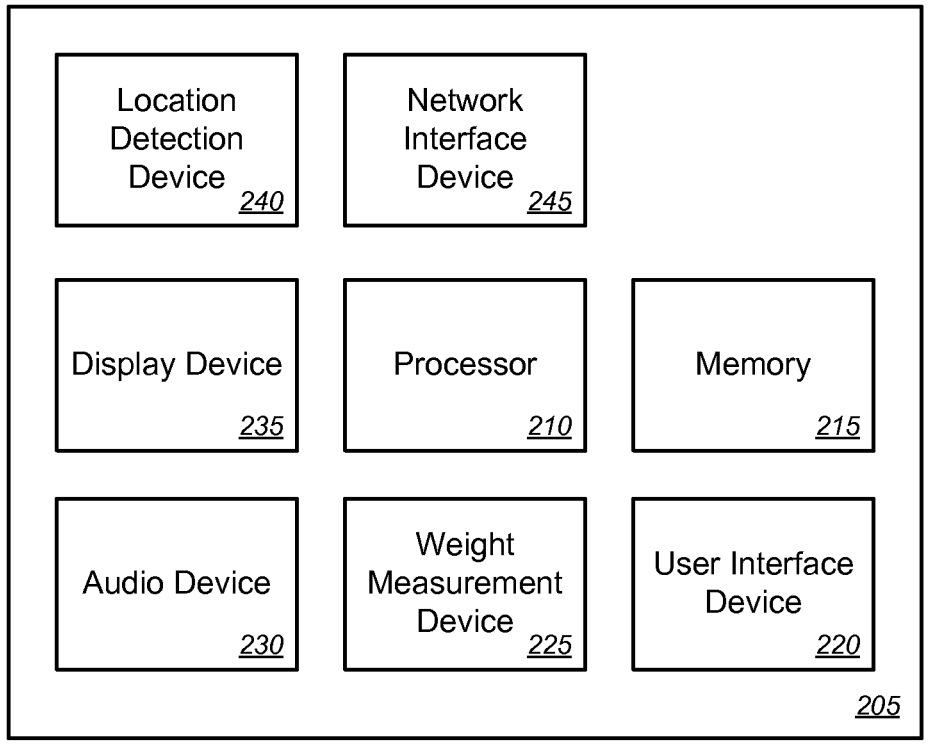

We now turn to FIGS. 2 and 3, which are directed to apparatuses 200 and/or configurations for implementing item or luggage loss prevention, in accordance with various embodiments. In particular, FIGS. 2A and 2B (collectively, "FIG. 2") are general block diagrams illustrating various apparatuses 200 for implementing item or luggage loss prevention, in accordance with various embodiments. FIGS. 3A-3F (collectively, "FIG. 3") are general schematic diagrams illustrating various placement and configurations for an apparatus for implementing item or luggage loss prevention, in accordance with various embodiments.

In FIG. 2A, apparatus 205, which corresponds to device 115 in FIG. 1 (as described in detail above), might comprise processor 210, memory 215, user interface device 220, weight measurement device 225, audio device 230, and/or display device 235. Memory 215 might store the notification preferences as well as one or more weights (or lock-in weights). User interface device 220 might comprise one or more touchscreen display devices, one or more buttons, one or more switches, or one or more light emitting devices. Weight measurement device 225 might comprise a load cell selected from a group consisting of a strain gauge load cell, a piezoelectric load cell, a capacitive load cell, a compression load cell, a compression/tension load cell, an S-beam load cell, a bending beam load cell, a platform load cell, a single point load cell, a canister load cell, and/or a low profile load cell. Audio device 230 might comprise, without limitation, one or more speakers, one or more tone generation devices, and/or the like. Display device 235 might comprise one or more light emitting devices, one or more touchscreen devices, one or more liquid crystal displays ("LCDs"), one or more light emitting diode ("LED") displays, one or more organic LED ("oLED") displays, and/or the like.

In FIG. 2B, another embodiment of apparatus 205 might further comprise one or more location detection devices 240 (which might include, without limitation, a GPS device, a location triangulation transceiver, and/or the like), one or more network interface devices 245 (which might include, but is not limited to, Bluetooth™ device, an 802.11 device, a WiFi device, a WiMax device, a WWAN device, cellular communication devices, and/or the like). Apparatuses 200 might function in a manner similar to device 115 described in detail above with respect to FIG. 1.

In FIG. 3, various different configurations and placement of a device 325 corresponding to device 115 or apparatus 200 are shown. As shown in FIG. 3, bag 205 might comprise one or more handles 310, one or more feet 315, and/or one or more wheel casters 320. Although FIG. 3 shows a particular type of bag, the various embodiments are not so limited, and the bag 305 can be any suitable bag including, without limitation, a purse, a handbag, a tote, a briefcase, a satchel, laptop bag, travel bag, carry-on luggage, and/or the like.

Figure 3A:
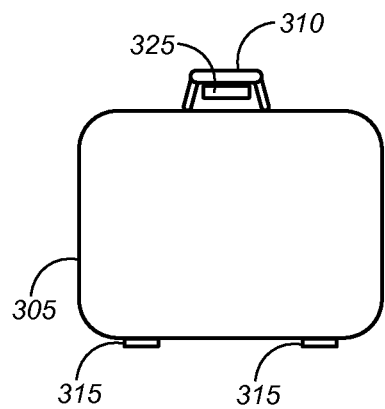
FIGS. 3A-3F are general schematic diagrams illustrating various placement and configurations for an apparatus for implementing item or luggage loss prevention, in accordance with various embodiments.

In the embodiment of FIG. 3A, device 325 might be affixed to at least an underside of the one or more handles 310. In particular, the weight measurement device 225 (shown in FIG. 2) might be placed under the one or more handles 310. In some embodiments, some portion of the device 325 (e.g., one or more of processor 210, memory 215, user interface device 220, audio device 230, display device 235, location detection device 240, and/or network interface device 245) might be positioned above the handles 310. In such a manner, these components may be protected against damage from constant lifting. Also, having the display device and the audio device on the upper side of the handles 310 might allow the user to better see and hear notifications through these components.

Figure 3B:
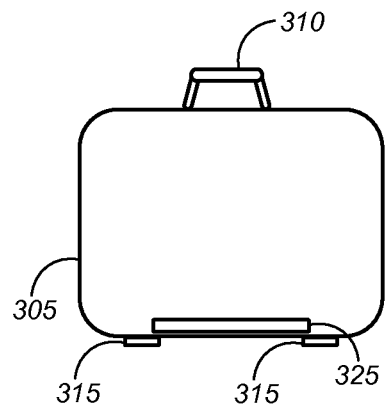
Figure 3C:
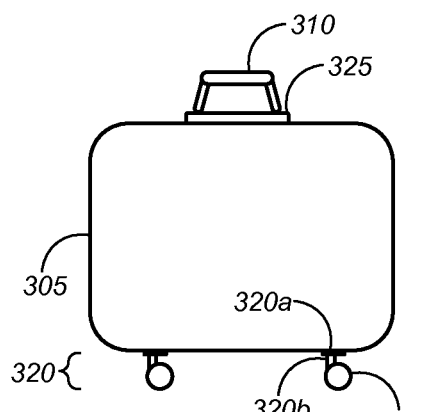

In the embodiment of FIG. 3B, device 325 might be placed at a bottom portion of an interior of the bag 305, ideally below where the one or more user devices (e.g., user devices 105 of FIG. 1) might be placed. In the embodiment of FIG. 3C, device 325 might be affixed or attached to the bag 305 between the bag 305 and the one or more handles 310.

Figure 3D:
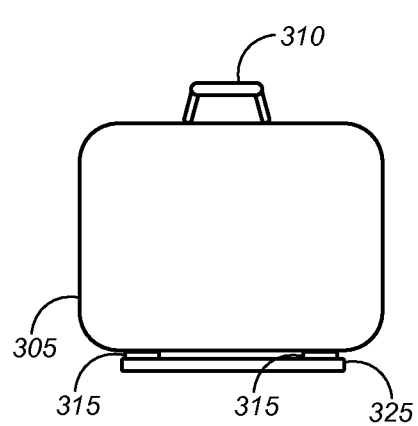
Figure 3E:
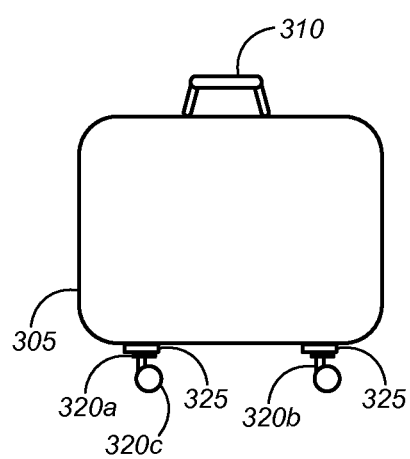
Figure 3F:
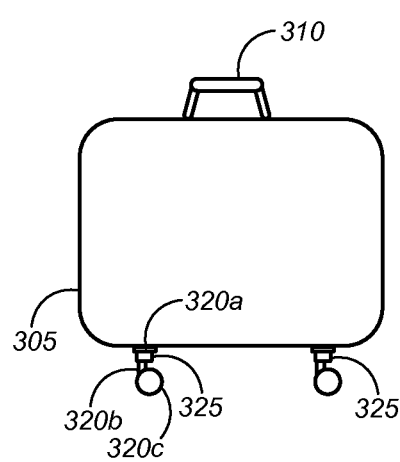

In the embodiment of FIG. 3D, device 325 might be affixed to the bottom of the one or more feet 315, while in the embodiment of FIG. 3E, the devices 325 might be affixed or attached to the bag 305 between the bag 305 and the one or more wheel casters 320. Alternatively, as shown in the embodiment of FIG. 3F, device 325 might be part of each of the wheel casters 320, where each device 325 might be positioned between the base 320a and the body 320b of each wheel casters 320, above the wheels 320c.

In the case of embodiments shown in FIGS. 3A and 3C, weight measurements must be taken while the corresponding bags 305 are being lifted. In the embodiment of FIG. 3B, weight measurements may be taken when the bag 305 is being lifted and when it is resting on a surface (e.g., ground, seat, table, etc.). For the embodiments shown in FIGS. 3D-3F, weight measurements may be taken when the bags are resting on a surface (e.g., ground, seat, table, etc.).

With reference to FIGS. 4A-4F (collectively, "FIG. 4"), which are general schematic diagrams illustrating various views and configurations of an apparatus 400 for implementing item or luggage loss prevention, in accordance with various embodiments. FIGS. 4A-4C show side views of apparatus 400, in which FIGS. 4A and 4C show partial cut-out views of portions of the apparatus 400. FIG. 4D shows a partial sectional view of portions of the apparatus 400 as seen along the direction of the A-A arrows in FIG. 4B, while FIG. 4E shows a partial sectional view of portions of the apparatus 400 as seen along the direction of the B-B arrows in FIG. 4B; in FIG. 4E, partial sectional view of contact surface 440 is shown as a small circle for ease of illustration particularly as compared with surrounding components and elements of the apparatus 400 (and not intended as an accurate sectional or partial section view of contact surface 440). FIG. 4F shows a different embodiment of apparatus 400. In FIG. 4, dash-lines or dotted-lines might denote cut-out or partial cut-out portions.

In FIG. 4, apparatus 400 might comprise a main body portion 405 and a piston portion 410. The main body portion 405 might comprise a shell portion 415 and first attachment portion 420. The shell portion 415 might comprise a first cap portion 415a and a second cap portion 415b. The first attachment portion 420 might attach to the first cap portion. The second cap portion is shown in greater detail in FIGS. 4D and 4E (and is described further below). According to some embodiments, the first attachment portion 420 might comprise one of a strap, a handle, and/or a resilient loop, each of which might be made of any suitable material including, but not limited to, metal, rubber, cloth, plastic, silicone, wood, or the like, and/or any combination of these materials.

The piston portion 410 might comprise a first attachment brace 425a, a second attachment brace 425b, a second attachment portion 430, and at least one rod 435. The first attachment brace 425a might include contact surface 440, which might comprise any suitable contact point including, but not limited to, a hemispheric contact point, a cubic contact point, a rectangular box contact point, a ball contact point, and/or the like. In some embodiments, the second attachment portion 430 might comprise one of a strap, a handle, and/or a resilient loop, each of which might be made of any suitable material including, but not limited to, metal, rubber, cloth, plastic, silicone, wood, or the like, and/or any combination of these materials.

The apparatus 400 might further comprise a contact sensor 445, which may be either integrally formed with the second cap portion 415b or separately formed with respect to the second cap portion 415b (but later affixed to the second cap portion 415b, before assembly of the piston portion 410 within the main body portion 405). The apparatus 400 might further comprise a sensor cable 450 and an interface device 455. The sensor cable 450 might, in some cases, communicatively couple the contact sensor 445 with the interface device 455. The processing or calculation of the weight based on the applied force (and changes in units of measurement, taring (i.e., the process of accounting for weight of the luggage and/or other components from the gross weight to measure weight of specific item(s) in the luggage), and/or the like) may be performed by a processor that is either located in the contact sensor 445 and/or the interface device 455. According to some embodiments, the contact sensor 445 might include, without limitation, at least one of a flex sensor, a piezoelectric-based sensor, a compression-based sensor, a spring-based sensor, and/or the like.

The contact surface 440 may be made of any suitable material, including, without limitation, metal, rubber, cloth, plastic, silicone, wood, or the like, and/or any combination of these materials, so long as the material does not deform so much that accurate measurement of force of contact between the contact surface 440 and the contact sensor 445 cannot be made. In some cases, the contact surface 440 might be integrally formed with the first attachment brace 425*a* (and might be of the same material or different material from the material of the first attachment brace 425*a*). In some instances, the contact surface 440 might be separately formed from the first attachment brace 425*a* (and might be of the same material or different material from the material of the first attachment brace 425*a*), and might be assembled with the first attachment brace 425*a* prior to assembly in the main body portion 405.

In operation, one of the main body portion 405 or the piston portion 410 might be (removably or permanently) attached or affixed to a piece of luggage (e.g., bag 305 as shown in FIG. 3, or any other suitable type of baggage, or the like), while the other of the main body portion 405 or the piston portion 410 might be carried (i.e., manipulated) by a user. When no force is applied (or when not fully lifted), the contact surface 440 and the contact sensor 445 might be spaced apart (as shown in FIG. 4A). When the user-manipulated portion (i.e., one of the main body portion 405 or the piston portion 410) is lifted, however, the first attachment brace 425*a* (and the contact surface 440 that is attached thereto or is otherwise part thereof) might move toward the second cap portion 415*b* (and the contact sensor 445 that is attached thereto or is otherwise part thereof), until the contact surface 440 makes contact with the contact sensor 445 (as shown in FIG. 4C). When the relative positions of the main body portion 405 and the piston portion 410 have stabilized (i.e., as weight of the luggage and contents therein are applied), the contact surface 440 applies a proportional amount of force to the contact sensor 445, which is measured and eventually registered as weight (in a manner similar to that described with respect to FIGS. 1-3 and 5). The weight may, in some cases, be displayed on a display screen or display device of the interface device 455. In some embodiments, the weight might be sent wirelessly as a data packet (from the interface device 455 and/or from the contact sensor 445) to a user device (e.g., smart phone, laptop, television, and/or the like) to be displayed on a display screen of the user device.

In some embodiments, the interface device 455 might comprise one or more of a display screen to display computed/measured weight, a voice output device (e.g., a speaker or the like) to provide vocal (or simulated vocal) outputs of the computed/measured weight, buttons to allow the user to select options (e.g., to turn on/off the display, to turn on/off the vocal output device, to select unit of weight, to select options for storing weights, to send computed/measured weights or other stored values or data to another user device (including, but not limited to, a smart phone, a mobile phone, a tablet computer, a laptop computer, a desktop computer, a television, and/or the like), to a server, and/or the like)). In some cases, such as in embodiments where the one of the main body portion 405 or the piston portion 410 is (removably or permanently) attached or affixed to the piece of luggage, the interface device 455 might comprise attachment mechanisms that allow the interface device 455 to also be (removably or permanently) attached or affixed to the piece of luggage (ideally in a manner so as to be easily viewed and/or manipulated by the user). In some instances, the interface device 455 might be (removably or permanently) attached or affixed to some portion of the apparatus 400, including, without limitation, the first attachment portion 420, the second attachment portion 430, the first cap portion 415*a*, the second cap portion 415*b*, an exterior part of the shell portion 415, and/or the like. In a non-limiting example, FIG. 4F shows the interface device 455 (removably or permanently) attached or affixed to an exterior portion of the first cap portion 415*a* (along the side of the shell portion 415).

According to some embodiments, where the interface device 455 is permanently attached or affixed to an exterior portion of the apparatus 400 (including, without limitation, the first attachment portion 420, the second attachment portion 430, the first cap portion 415*a*, the second cap portion 415*b*, an exterior part of the shell portion 415, and/or the like), the sensor cable 450 might be routed within the shell portion 415. In some embodiments, where the interface device 455 is (removably or permanently) attached or affixed to a portion of the piece of luggage, or removably attached or affixed to an exterior portion of the apparatus 400 (including, without limitation, the first attachment portion 420, the second attachment portion 430, the first cap portion 415*a*, the second cap portion 415*b*, an exterior part of the shell portion 415, and/or the like), the sensor cable 450 might be routed through slot 460 (as shown in FIG. 4B).

In some cases, the at least one rod 435 might include one of two rods (as shown in FIG. 4), three rods (not shown), four rods (not shown), or any suitable number of rods. In some instances, the first attachment brace 425*a* and each of the at least one rod 435 might form a U-shaped brace (not shown), the "legs" of which might fit through the openings 465 in the second attachment brace 425*b*, while the "top" of the U-shaped brace might include contact surface 440. In some embodiments, the U-shaped brace might include, without limitation, one of a curved U-shaped brace, a flat U-shaped brace, or a curved W-shaped brace, and/or the like. The curved U-shaped brace might comprise a "top" of the U-shaped brace that is curved outward toward first cap portion 415*a* when the U-shaped brace is installed in the main body portion 405. The flat U-shaped brace might include a "top" of the U-shaped brace that is substantially perpendicular with the "legs" of the U-shaped brace. The curved W-shaped brace might have a "top" of the U-shaped brace that first curves outward toward the first cap portion 415*a* (when the U-shaped brace is installed in the main body portion 405) from each of the "legs," then curved inward away from the first cap portion 415*a* and toward the second cap portion 415*b* to meet in the middle (the overall shape of which evokes or resembles the letter W that has curvy connections). In some instances, the U-shaped brace might have a flat profile (i.e., instead of "rods" for legs, the "legs" might be flat rectangular pieces). In other cases, the U-shaped brace might have circular or oval cross-sections throughout (i.e., the "legs" and/or the "top" might be cylindrical or a bent cylinder, or the like).

FIGS. 4D and 4E show partial sectional views of apparatus 400 (along the A-A and B-B directions in FIG. 4B) that show how the piston portion 410 is connected or assembled with the main body portion 405. In particular, openings 465 (two in the case of the embodiment of FIG. 4D) are shown in the second cap portion 415*b*. The openings 465 (shown as being circular in FIGS. 4D and 4E) may be of whatever shape that matches with the shape of the at least one rod 435, so as to allow each of the at least one rod 435 to pass through each corresponding opening 465. The contact sensor 445, although shown as having circular cross section, can have a cross section having any suitable shape, including, but not limited to, circle, square, triangle, rectangle, any polygon, or any irregular shape, and/or the like. Likewise, the contact surface 440, although shown as having circular cross section, can have a cross section having any suitable shape, including, but not limited to, circle, square, triangle, rectangle, any polygon, or any irregular shape, and/or the like. In general, however, the shapes of the contact sensor 445 and the contact surface 440 are chosen to complement each other (although not necessarily having the same shape) to ensure proper mutual contact to afford accurate force/weight measurements.

In some instances, one of the first attachment portion 420 or the second attachment portion 430 might include, without limitation, a handle, strap, or bar that is configured to be held with a user's hand(s), while the other of the first attachment portion 420 or the second attachment portion 430 might include, but is not limited to, a handle, strap, or bar that is configured to be (removably or permanently) attached or affixed to a piece of luggage. In some embodiments, the other of the first attachment portion 420 or the second attachment portion 430 (i.e., the luggage-side attachment portion) might include, without limitation, a releasable engagement device 470, which might include (but is not limited) to one of a clasp, a buckle, a carabiner, a clip, or any other suitable fastener, or the like. The releasable engagement device 470 might be made of any suitable material including, without limitation, metal, plastic, and/or the like. In operation, the clasp-type or buckle-type engagement devices 470 might be separable into two portions, a first portion attached or affixed to a first part of the luggage-side attachment portion and a second portion attached or affixed to a second part of the luggage-side attachment portion. In some cases, as shown in the non-limiting example of FIG. 4F, the first part 430' of the luggage-side portion might be longer than the second part 430" of the luggage-side portion, with the engagement device 470 removably coupling the first part 430' to the second part 430". The longer first part 430' allows the luggage-side portion to loop about a handle or other loop-type structure on the piece of luggage, and to allow the weight of the handle or other loop-type structure on the piece of luggage to be held against the first part 430' without the weight of the luggage pressing against (and potentially damaging) the engagement device 470.

In some cases, the apparatus 400 (including each of the main body portion 405 and the piston portion 410) might be cylindrical in shape. In other cases, the apparatus 400 (including each of the main body portion 405 and the piston portion 410) might be rectangular in shape. While in still other cases, the apparatus 400 (including each of the main body portion 405 and the piston portion 410) might be any suitable shape. In some embodiments, any edges and/or any corners may be made to be rounded.

Although FIG. 4 shows the contact surface 440 attached or affixed to the piston portion 410 while the contact sensor 445 is shown attached or affixed to the main body portion 405, the various embodiments are not so limited, and the contact surface 440 attached or affixed to the main body portion 405 while the contact sensor 445 is shown attached or affixed to the piston portion 410.

Figure 5:
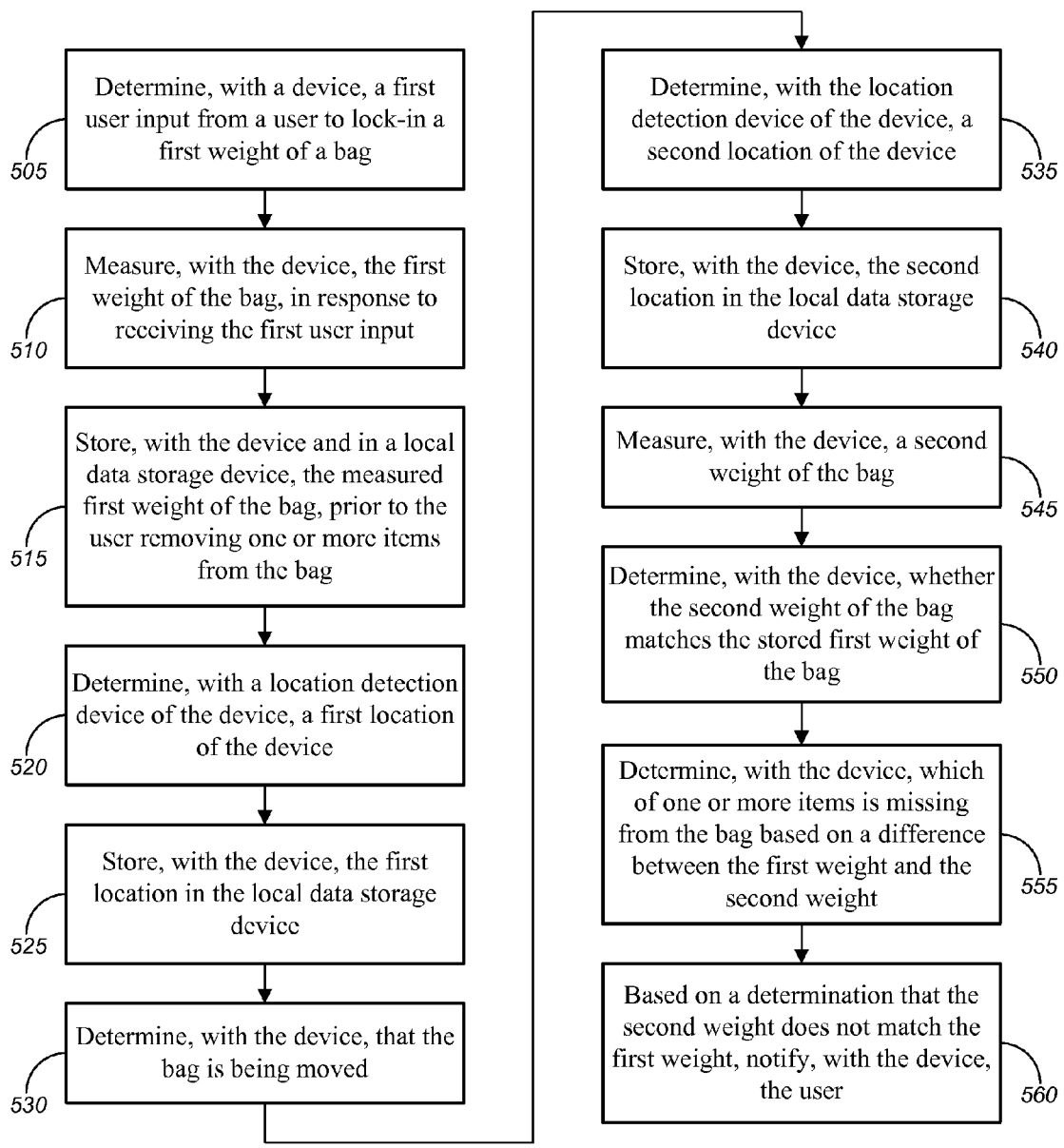
FIG. 5 is a general schematic flow diagram illustrating a method for implementing item or luggage loss prevention, in accordance with various embodiments.

We now turn to FIG. 5, which is a general schematic flow diagram illustrating a method 500 for implementing item or luggage loss prevention, in accordance with various embodiments. While the techniques and procedures of the method 500 is depicted and/or described in a certain order for purposes of illustration, it should be appreciated that certain procedures may be reordered and/or omitted within the scope of various embodiments. Moreover, while the method illustrated by FIG. 5 can be implemented by (and, in some cases, are described below with respect to) systems 100 of FIG. 1 (or components thereof), apparatus 200 of FIG. 2, apparatus 325 of FIG. 3, and/or apparatus 400 of FIG. 4, the method may also be implemented using any suitable hardware implementation. Similarly, while system 100 (and/or components thereof) can operate according to the method illustrated by FIG. 5 (e.g., by executing instructions embodied on a computer readable medium), system 100 can also operate according to other modes of operation and/or perform other suitable procedures.

In FIG. 5, method 500 might comprise, at block 505, determining, with a device, a first user input from a user to lock-in a first weight of a bag. Method 500 might further comprise measuring, with the device, the first weight of the bag, in response to receiving the first user input (block 510). At block 515, method 500 might comprise storing, with the device and in a local data storage device, the measured first weight of the bag, prior to the user removing one or more items from the bag.

In some embodiments, particular where the device might comprise a location detection device (such as location detection device 240 shown in FIG. 2), method 500 might, at block 520, comprise determining, with the location detection device of the device, a first location of the device (e.g., when measuring the first weight of the bag). At block 525, method 500 might comprise storing, with the device, the first location in the local data storage device.

Method 500 might further comprise determining, with the device, that the bag is being moved (block 530). In some cases, this might comprise determining, with the location detection device of the device, a second location of the device when measuring the second weight of the bag (block 535), storing, with the device, the second location in the local data storage device (block 540), and determining, with the device, that the second location is different from the first location.

At block 545, method 500 might comprise measuring, with the device, a second weight of the bag. In some cases, this second measurement might be performed in response to determining that the bag is being moved. In other cases, the second measurement might be performed in response to another triggering event (e.g., user input requesting the weight of the bag) and/or the measurement might be performed periodically.

Method 500, at block 550, might comprise determining, with the device, whether the second weight of the bag matches the stored first weight of the bag. In some embodiments, method 500 might comprise, at block 555, determining, with the device, which of one or more items (including, without limitation, laptops, smart phones, tablet computers, cellular phones, media players, and/or the like) is missing from the bag based on a difference between the first weight and the second weight. This might include pre-storing a plurality of weights of the bag, with and without each of the one or more items.

Based on a determination that the second weight does not match the first weight, method 500 might comprise notifying, with the device, the user (block 560). In some embodiments, notifying the user might comprise one or more of playing a recorded voice notification, emitting one or more audio tones, displaying one or more light sequences, displaying one or more icons, displaying a written message, sending an e-mail notification, sending a text message notification, sending a small message service ("SMS") notification, sending a multi-media messaging service ("MMS") notification, or sending a chat message notification.

Figure 6:
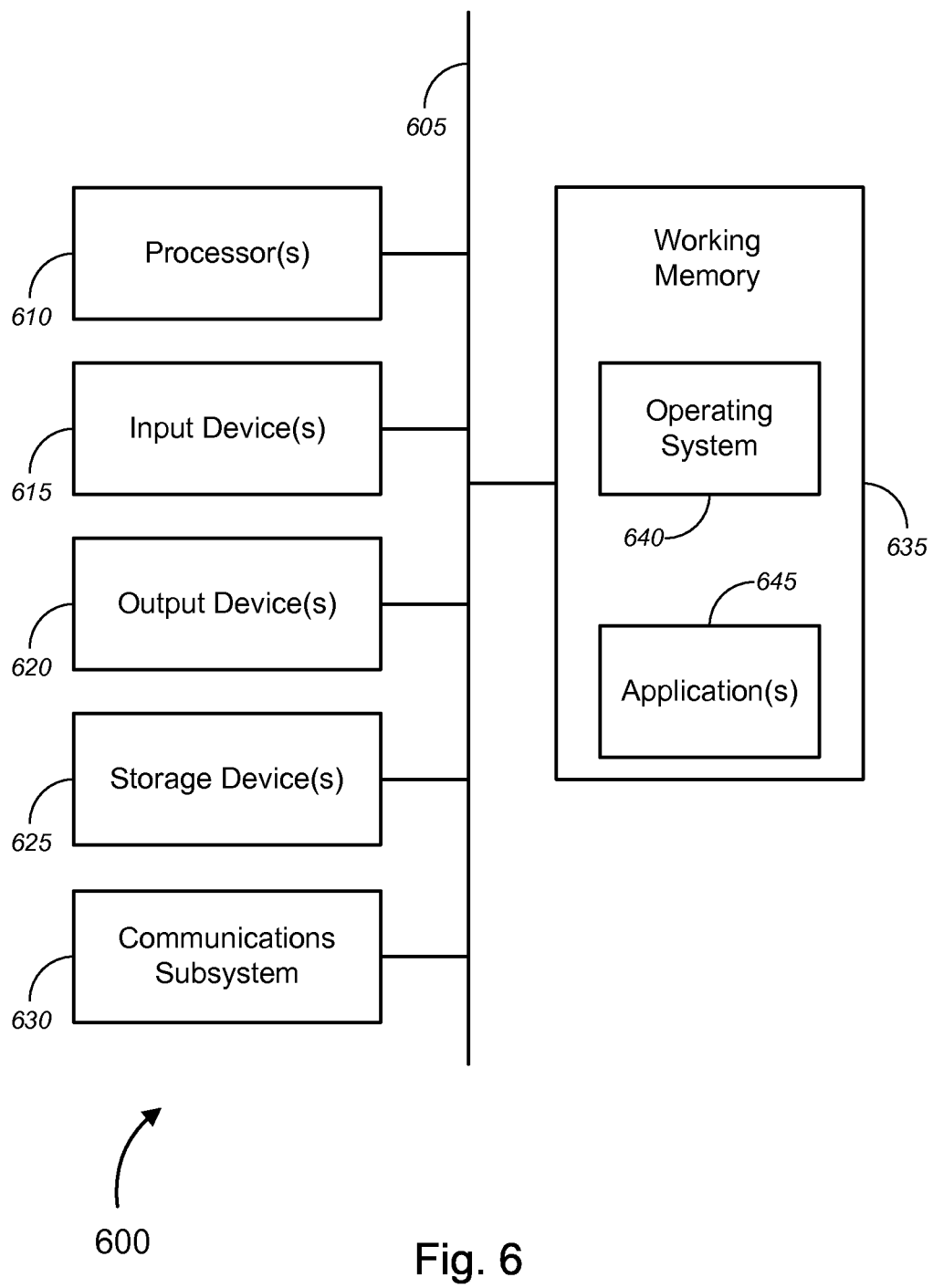
FIG. 6 is a block diagram illustrating an exemplary computer architecture, in accordance with various embodiments.

We now turn to FIG. 6, which is a block diagram illustrating an exemplary computer architecture. FIG. 6 provides a schematic illustration of one embodiment of a computer system 600 that can perform the methods provided by various other embodiments, as described herein, and/or can perform the functions of local computer system 115, 205, 325, or 400, or remote computer system 120, or other computer systems as described above. It should be noted that FIG. 6 is meant only to provide a generalized illustration of various components, of which one or more, or none, of each may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605, or may otherwise be in communication, as appropriate. The hardware elements may include one or more processors 610, including without limitation one or more general-purpose processors, or one or more special-purpose processors such as digital signal processing chips, graphics acceleration processors, or the like; one or more input devices 615, which can include without limitation a mouse, a keyboard, or the like; and one or more output devices 620, which can include without limitation a display device, a printer, or the like.

The computer system 600 may further include, or be in communication with, one or more storage devices 625. The one or more storage devices 625 can comprise, without limitation, local and/or network accessible storage, or can include, without limitation, a disk drive, a drive array, an optical storage device, a solid-state storage device. The solid-state storage device can include, but is not limited to, one or more of a random access memory ("RAM") or a read-only memory ("ROM"), which can be programmable, flash-updateable, or the like. Such storage devices may be configured to implement any appropriate data stores, including without limitation various file systems, database structures, or the like.

The computer system 600 might also include a communications subsystem 630, which can include without limitation a modem, a network card (wireless or wired), an infra-red communication device, a wireless communication device or chipset, or the like. The wireless communication device might include, but is not limited to, a Bluetooth™ device, an 802.11 device, a WiFi device, a WiMax device, a WWAN device, cellular communication facilities, or the like.

The communications subsystem 630 may permit data to be exchanged with a network (such as network 125, to name an example), with other computer systems, with any other devices described herein, or with any combination of network, systems, and devices. According to some embodiments, network 125 might include a local area network ("LAN"), including without limitation a fiber network, an Ethernet network, a Token-Ring™ network, and the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol, or any other wireless protocol; or any combination of these or other networks. In many embodiments, the computer system 600 will further comprise a working memory 635, which can include a RAM or ROM device, as described above.

The computer system 600 may also comprise software elements, shown as being currently located within the working memory 635, including an operating system 640, device drivers, executable libraries, or other code. The software elements may include one or more application programs 645, which may comprise computer programs provided by various embodiments, or may be designed to implement methods and/or configure systems provided by other embodiments, as described herein. Merely by way of example, one or more procedures described with respect to the methods discussed above might be implemented as code or instructions executable by a computer or by a processor within a computer. In an aspect, such code or instructions can be used to configure or adapt a general purpose computer, or other device, to perform one or more operations in accordance with the described methods.

A set of these instructions or code might be encoded and/or stored on a non-transitory computer readable storage medium, such as the storage devices 625 described above. In some cases, the storage medium might be incorporated within a computer system, such as the system 600. In other embodiments, the storage medium might be separate from a computer system—that is, a removable medium, such as a compact disc, or the like. In some embodiments, the storage medium might be provided in an installation package, such that the storage medium can be used to program, configure, and/or adapt a general purpose computer with the instructions/code stored thereon. These instructions might take the form of executable code, which is executable by the computer system 600, or might take the form of source or installable code. The source or installable code, upon compilation, installation, or both compilation and installation, on the computer system 600 might take the form of executable code. Compilation or installation might be performed using any of a variety of generally available compilers, installation programs, compression/decompression utilities, or the like.

It will be apparent to those skilled in the art that substantial variations may be made in accordance with specific requirements. For example, customized hardware—such as programmable logic controllers, field-programmable gate arrays, application-specific integrated circuits, or the like—might also be used. In some cases, particular elements might be implemented in hardware, software (including portable software, such as applets, etc.), or both. Further, connection to other computing devices such as network input/output devices may be employed.

As mentioned above, in one aspect, some embodiments may employ a computer system, such as the computer system 600, to perform methods in accordance with various embodiments of the invention. According to a set of embodiments, some or all of the procedures of such methods might be performed by the computer system 600 in response to processor 610 executing one or more sequences of one or more instructions. The one or more instructions might be incorporated into the operating system 640 or other code that may be contained in the working memory 635, such as an application program 645. Such instructions may be read into the working memory 635 from another computer readable medium, such as one or more of the storage devices 625. Merely by way of example, execution of the sequences of instructions contained in the working memory 635 might cause the one or more processors 610 to perform one or more procedures of the methods described herein.

The terms "machine readable medium" and "computer readable medium," as used herein, refer to any medium that participates in providing data that causes a machine to operate in a specific fashion. In an embodiment implemented using the computer system 600, various computer readable media might be involved in providing instructions or code to the one or more processors 610 for execution, might be used to store and/or carry such instructions/code such as signals, or both. In many implementations, a computer readable medium is a non-transitory, physical, or tangible storage medium. Such a medium may take many forms, including, but not limited to, non-volatile media, volatile media, and transmission media. Non-volatile media includes, for example, optical disks, magnetic disks, or both, such as the storage devices 625. Volatile media includes, without limitation, dynamic memory, such as the working memory 635. Transmission media includes, without limitation, coaxial cables, copper wire and fiber optics, including the wires that comprise the bus 605, as well as the various components of the communication subsystem 630, or the media by which the communications subsystem 630 provides communication with other devices. Hence, transmission media can also take the form of waves, including without limitation radio, acoustic, or light waves, such as those generated during radio-wave and infra-red data communications.

Common forms of physical or tangible computer readable media include, for example, a floppy disk, a flexible disk, a hard disk, magnetic tape, or any other magnetic medium; a CD-ROM, DVD-ROM, or any other optical medium; punch cards, paper tape, or any other physical medium with patterns of holes; a RAM, a PROM, an EPROM, a FLASH-EPROM, or any other memory chip or cartridge; a carrier wave; or any other medium from which a computer can read instructions or code.

Figure 7:
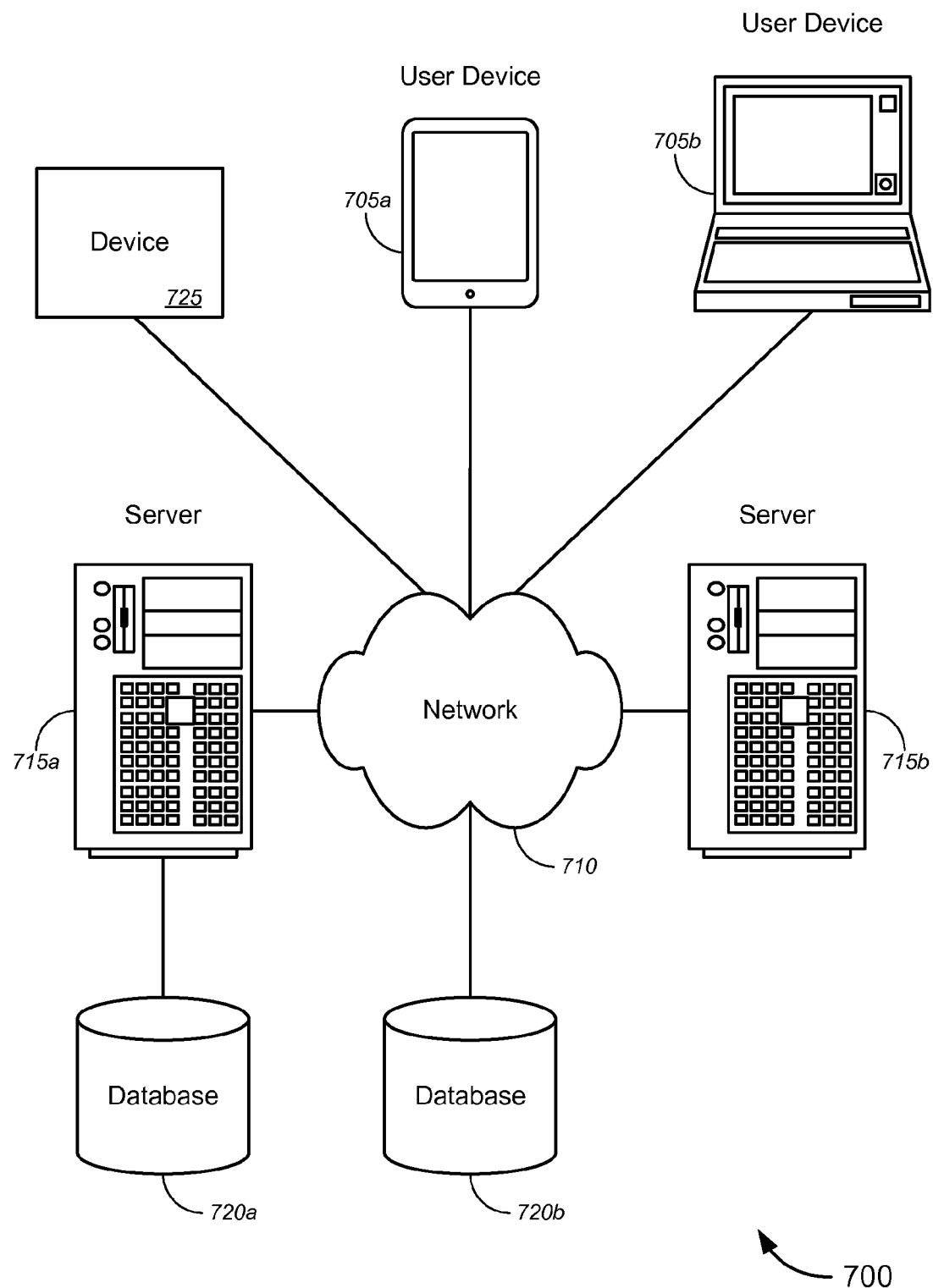
FIG. 7 is a block diagram illustrating a networked system of computers, which can be used in accordance with various embodiments.

As noted above, a set of embodiments comprises methods and systems for implementing item or luggage loss prevention. FIG. 7 illustrates a schematic diagram of a system 700 that can be used in accordance with one set of embodiments. The system 700 can include one or more user computers or user devices 705. A user computer or user device 705 can be a general purpose personal computer (including, merely by way of example, desktop computers, tablet computers, laptop computers, handheld computers, and the like, running any appropriate operating system, several of which are available from vendors such as Apple, Microsoft Corp., and the like) and/or a workstation computer running any of a variety of commercially-available UNIX™ or UNIX-like operating systems. A user computer or user device 705 can also have any of a variety of applications, including one or more applications configured to perform methods provided by various embodiments (as described above, for example), as well as one or more office applications, database client and/or server applications, and/or web browser applications. Alternatively, a user computer or user device 705 can be any other electronic device, such as a thin-client computer, Internet-enabled mobile telephone, and/or personal digital assistant, capable of communicating via a network (e.g., the network 710 described below) and/or of displaying and navigating web pages or other types of electronic documents. Although the exemplary system 700 is shown with two user computers or user devices 705, any number of user computers or user devices can be supported.

Certain embodiments operate in a networked environment, which can include a network 710. The network 710 can be any type of network familiar to those skilled in the art that can support data communications using any of a variety of commercially-available (and/or free or proprietary) protocols, including without limitation TCP/IP, SNA™, IPX™, AppleTalk™, and the like. Merely by way of example, the network 710 can include a local area network ("LAN"), including without limitation a fiber network, an Ethernet network, a Token-Ring™ network and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 715. Each of the server computers 715 may be configured with an operating system, including without limitation any of those discussed above, as well as any commercially (or freely) available server operating systems. Each of the servers 715 may also be running one or more applications, which can be configured to provide services to one or more clients 705 and/or other servers 715.

Merely by way of example, one of the servers 715 might be a data server, as described above. The data server might include (or be in communication with) a web server, which can be used, merely by way of example, to process requests for web pages or other electronic documents from user computers 705. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 705 to perform methods of the invention.

The server computers 715, in some embodiments, might include one or more application servers, which can be configured with one or more applications accessible by a client running on one or more of the client computers 705 and/or other servers 715. Merely by way of example, the server(s) 715 can be one or more general purpose computers capable of executing programs or scripts in response to the user computers 705 and/or other servers 715, including without limitation web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including without limitation those commercially available from Oracle™, Microsoft™, Sybase™' IBM™ and the like, which can process requests from clients (including, depending on the configuration, dedicated database clients, API clients, web browsers, etc.) running on a user computer or user device 705 and/or another server 715. In some embodiments, an application server can perform one or more of the processes for implementing automated cloud expansion and ordering, or the like, as described in detail above. Data provided by an application server may be formatted as one or more web pages (comprising HTML, JavaScript, etc., for example) and/or may be forwarded to a user computer 705 via a web server (as described above, for example). Similarly, a web server might receive web page requests and/or input data from a user computer 705 and/or forward the web page requests and/or input data to an application server. In some cases a web server may be integrated with an application server.

In accordance with further embodiments, one or more servers 715 can function as a file server and/or can include one or more of the files (e.g., application code, data files, etc.) necessary to implement various disclosed methods, incorporated by an application running on a user computer 705 and/or another server 715. Alternatively, as those skilled in the art will appreciate, a file server can include all necessary files, allowing such an application to be invoked remotely by a user computer or user device 705 and/or server 715.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 720. The location of the database(s) 720 is discretionary: merely by way of example, a database 720a might reside on a storage medium local to (and/or resident in) a server 715a (and/or a user computer or user device 705). Alternatively, a database 720b can be remote from any or all of the computers 705, 715, so long as it can be in communication (e.g., via the network 710) with one or more of these. In a particular set of embodiments, a database 720 can reside in a storage-area network ("SAN") familiar to those skilled in the art. (Likewise, any necessary files for performing the functions attributed to the computers 705, 715 can be stored locally on the respective computer and/or remotely, as appropriate.) In one set of embodiments, the database 720 can be a relational database, such as an Oracle database, that is adapted to store, update, and retrieve data in response to SQL-formatted commands. The database might be controlled and/or maintained by a database server, as described above, for example.

According to some embodiments, the system can further include device 725, which is configured to be attached to and/or placed in a bag (including, without limitation, a purse, a handbag, a tote, a briefcase, a satchel, laptop bag, travel bag, carry-on luggage, and/or the like). In some cases, device 725 is an item or luggage loss prevention device that is weight-measurement-based, as described in detail above with respect to FIGS. 1-5. In other words, device 725 might correspond with, and might have functionalities that are similar to, devices 115, 205, 325, and 400 as described in detail with respect to FIGS. 1-4.

Although the above embodiments specifically identify electronics components as items that can be tracked (by weight) to prevent loss, the various embodiments are not so limited, and other items may be similarly tracked. Such other items might include, without limitation, eye wear, time pieces (e.g., watches, stopwatches, etc.), jewelry, clothing (ideally, heavier articles of clothing), gifts, toiletry, personal hygiene products, and/or the like.

In some embodiments, the systems, apparatuses, and/or methods described above may be applied to child safety seats or child seats. For example, with reference to the embodiments of FIG. 3, device 325 (or similar device) may be affixed to at least an underside of a handle of the child seat (so that when positioned from a stored position to a carrying position, relative to the body of the child seat, the device is positioned on at least the underside of the handle), not unlike the relative positioning as shown in FIG. 3A. In some cases, some portion of the device 325 (e.g., one or more of processor 210, memory 215, user interface device 220, audio device 230, display device 235, location detection device 240, and/or network interface device 245) might be positioned above the handles, not unlike the embodiment of FIG. 3A. In some instances, device 325 (or similar device) might be affixed or attached to the child seat between the child seat and the handle (e.g., a hinge joint or other suitable connection joint, or the like), not unlike the embodiment of FIG. 3C.

In some cases, device 325 (or similar device) might be placed at a bottom portion of a child seat—for example, between a bottom shell portion and bottom inner cushions (i.e., the part on which a baby's body may be set to rest) of the child seat, not unlike the embodiment of FIG. 3B. Alternatively, device 325 (or similar device) might be placed below the bottom shell portion of the child seat (i.e., below the feet of the child seat, if any), not unlike the embodiment of FIG. 3D. In some instances, if the child seat has feet or wheels, device 325 (or similar device) might be placed between the bottom shell portion of the child seat and the feet or wheels of the child seat, not unlike the embodiment of FIG. 3E, or as part of the feet or wheels of the child seat, not unlike the embodiment of FIG. 3F.

Merely by way of example, for compression-based weight sensing, such as shown in the embodiments of FIG. 3A, 3B, or 3D-3F, the device 325 (or similar device) might comprise a contact surface (e.g., contact surface 440, or the like) and a contact sensor (e.g., contact sensor 445, or the like). The contact surface and the contact sensor are configured so as to be spaced apart when not sensing—which, in some embodiments, may be accomplished with the use of springs, gravity, or the like. Where springs are used, the sensor might be calibrated to take into account the spring constant and other properties of the spring and/or connection configurations when calculating or measuring weight. The contact sensor, like that in the embodiment of FIG. 4, might communicatively couple to an interface device (e.g., interface device 455) via a cable (e.g., sensor cable 450). A processor (located either in the contact sensor or the interface device) might perform processing or calculation of the weight based on the applied force. In some cases, the interface device might couple to a network interface device and/or location detection device, and might allow sending of notifications, alerts, or messages to user devices associated with the parents or guardians of the baby if the baby is missing, in danger, or otherwise. The location detection might help parents or guardians in determining where the child was last in the child seat, which may help in locating a missing baby. In some embodiments, multiple devices may be used for each child seat, e.g., to provide more nuanced weight measurements (e.g., for detecting problems or issues that the baby might encounter, as described below).

For tension-based weight sensing, such as shown in the embodiments of FIG. 3C or 4, the apparatus 400 (or similar apparatus) may be used, in a manner as described above with respect to FIGS. 3C and 4. In some cases, the child seat might have an outer shell housing and an inner shell housing. The inner shell housing might have the cushion and the like on which the baby may be set to rest, while the outer shell housing is designed to rest on a surface (e.g., seat of a car, a table, a bed, a ground surface, or a frame for a baby stroller, and/or the like). In some embodiments, the outer shell housing might have a lip or wall that extends upward to encompass at least a portion of an exterior lip or wall of the inner shell housing, and the child seat might comprise two or more (e.g., three or four) connection apparatuses, not unlike apparatus 400 that connects or couples the inner shell housing to the outer shell housing. In some cases, the outer shell housing lip or wall might be vertically aligned with the at least a portion of the exterior lip or wall of the inner shell housing, although such configuration is not necessary for achieving the functionalities described herein. In one set of embodiments, for each of the connection apparatuses, the outer shell housing might be connected to first attachment portion (e.g., first attachment portion 420 or the like), while the inner shell housing might be connected to second attachment portion (e.g., second attachment portion 430 or the like). In this manner, the inner shell housing is almost always hanging from the outer shell housing. The tension-based weight sensing embodiments are otherwise similar, if not identical, to the compression-based weight sensing embodiments, and descriptions of the compression-based weight sensing embodiments are similarly applicable to those of the tension-based weight sensing embodiments.

With the systems, apparatuses, and methods described above, it is made possible to ensure that a baby is not left behind, such as when absent-minded and rushed parents or guardians are packing luggage and/or other children for a trip and potentially, accidentally leaving the baby behind (thinking that the baby is securely fastened in the child seat). This might be exacerbated by child seat covers or blankets for keeping the baby warm (such covers or blankets might obscure one's view of the presence or absence of the baby). With the systems, apparatuses, and methods described above, it may easily be determined that the baby is absent, and, in some cases, a notification (e.g., sound notification, e-mail notification, text/chat message notification, voice recording notification, and/or the like) might alert the parents or guardians of this fact (in some cases, by sending such notification to a mobile device(s) associated with the parents or guardians). In some instances, a proximity or motion sensor on the child seat might determine whether a parent or other persons are moving away from the child seat, and might send such information to a processor (e.g., processor 210). In some cases, the proximity sensor might track proximity (and/or movement relative) to a mobile device(s) associated with the parents or guardians of the child. If the processor determines that the proximity or motion sensor data indicate that a parent or other persons have moved away from the child seat by a certain (predetermined or preset) distance while the child seat is occupied by a child (e.g., by receiving weight and weight change data indicating that the child is in the child seat, etc.), regardless of whether the child seat is in a vehicle, at home, or in some other location, then the processor might send a notification (e.g., sound notification, e-mail notification, text/chat message notification, voice recording notification, and/or the like) of such fact to the mobile device(s) associated with the parents or guardians. In some instances, such notification can warn the parents or guardians when the child seat with the child in it has been moved away from them (either inadvertently or purposefully) by some other person.

In other embodiments, the systems, apparatuses, and methods described above might determine that the baby has somehow gotten out of the child seat, and may alert the parents or guardians of such an event (in some cases, by sending a notification to the mobile device(s) associated with the parents or guardians). In yet other embodiments, systems, apparatuses, and methods described above might determine that something is amiss with the baby (including, but not limited to, the baby is too still for too long, the weight distribution of the baby is not normal, excess weight is detected, and/or the like), which might indicate urgent (and potentially serious or dangerous) issues have arisen with respect to the baby (e.g., the baby is either in deep sleep or not breathing, the baby is in an odd position that might harm the baby, something has fallen on the child seat and/or the baby, and/or the like). In some cases, with the constant or near constant weight measurement, and with appropriate storage devices installed or frequent sending of weight information to an external storage device, the baby's weight can be tracked over time to give the parents, guardians, or pediatrician a record of the baby's growth.

Although applications related to babies are described above with respect to child seats, other appliances or such may also be configured to use the systems, apparatuses, and/or methods described herein. For example, bassinets (where stationary, rocking, hanging, or the like) may be modified (or designed) to utilize the systems, apparatuses, and/or methods herein, in a manner similar to those as described above with respect to the child seats. With such modified (or designed) bassinets, it can be determined when and if the baby has fallen out, has crawled out, has climbed out, or has been taken out, or the like. It can also be determined if, when, and for how long the baby has not been too still for too long, or if, when, and for how long an abnormal weight distribution of the baby is detected. It can be determined if, when, and for how long an excess weight is detected (e.g., suddenly detected). And so on. These and other weight-based or weight determined issues may be determined, and notifications of such may be sent to parents, guardians, and/or pediatricians (or the parents, guardians, and/or pediatricians are otherwise alerted of such issues) as necessary or desired. As with the child seat, the baby's weight can be tracked to allow recording of the baby's growth over time.

These and other similar systems, apparatuses, and methods may be similarly applicable to pet carriers, pet mats (or mattresses) in vehicles, pet mats (or mattresses) at home, and/or the like, in order to provide similar information to pet owners about their pets. For outdoor sports enthusiasts, similar technology may be applied to vehicle parts to alert people of missing bicycles, kayaks, canoes, rafts, snowboards, skis, trailers, and/or the like. The various embodiments are not limited to these specific embodiments described herein, and may be applied to other situations and uses, as ordinary (or skilled) person can appreciate.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
    receiving, with a device, a first user input from a user to lock-in a first weight of a bag;
    measuring, with the device, the first weight of the bag, in response to receiving the first user input;
    storing, with the device and in a local data storage device, the measured first weight of the bag, prior to the user removing one or more items from the bag;
    determining, with a location detection device of the device, a first location of the device when measuring the first weight of the bag;
    storing, with the device, the first location in the local data storage device;
    determining that the bag is being moved by determining, with the location detection device, that a present location of the device is different from the first location of the device;
    based on a determination by the location detection device that the bag is being moved, measuring, with the device, a second weight of the bag and determining, with the device, whether the second weight of the bag matches the stored first weight of the bag; and
    based on a determination that the second weight does not match the first weight, notifying, with the device, the user.

2. The method of claim 1, wherein the device is attached to the bag.

3. The method of claim 2, wherein the device is attached to one or more handles of the bag.

4. The method of claim 1, wherein the device is placed in an interior compartment of the bag.

5. The method of claim 4, wherein the device is placed at a bottom portion of the interior compartment of the bag.

6. The method of claim 1, wherein the device is placed below one or more feet of the bag.

7. The method of claim 1, wherein the device is affixed to a position between the bag and each of one or more wheel casters of the bag.

8. The method of claim 1, wherein the device is positioned within a one or more wheel casters of the bag.

9. The method of claim 1, wherein the bag comprises one or more of a purse, a handbag, a tote, a briefcase, a satchel, laptop bag, travel bag, or carry-on luggage.

10. The method of claim 1, wherein measuring each of the first weight and the second weight comprises measuring using a weight measurement device comprising a load cell selected from a group consisting of a strain gauge load cell, a piezoelectric load cell, a capacitive load cell, a compression load cell, a compression/tension load cell, an S-beam load cell, a bending beam load cell, a platform load cell, a single point load cell, a canister load cell, and a low profile load cell.

11. The method of claim 10, further comprising:
    determining that the bag is being moved by determining, with the device, that the load cell of the weight measurement device is being actuated.

12. The method of claim 1, wherein measuring each of the first weight and the second weight comprises measuring using a weight measurement device comprising a contact surface and a contact sensor, wherein the weight measurement device has a structure that causes the contact surface to be brought into contact with the contact sensor when a first portion of the weight measurement device is lifted with respect to a second portion of the weight measurement device, which is coupled to the bag.

13. The method of claim 12, wherein the contact sensor comprises at least one of a flex sensor, a piezoelectric-based sensor, a compression-based sensor, or a spring-based sensor.

14. The method of claim 1, wherein determining that the second weight does not match the first weight comprises determining that the second weight is less than the first weight.

15. The method of claim 1, wherein determining that the second weight does not match the first weight comprises determining that the second weight is greater than the first weight, wherein notifying the user comprises reminding the user to check that the one or more items that were removed from the bag have been returned to the bag.

16. The method of claim 1, further comprising:
    determining, with the location detection device of the device, a second location of the device when measuring the second weight of the bag;
    storing, with the device, the second location in the local data storage device;
    wherein notifying the user comprises sending a message containing each location where a weight of the bag was measured.

17. The method of claim 1, further comprising:
    determining, with the device, which of one or more items is missing from the bag based on a difference between the first weight and the second weight;
    wherein notifying the user comprises indicating which of the one or more items might be missing based on the determination.

18. The method of claim 1, wherein notifying the user comprises one or more of playing a recorded voice notification, emitting one or more audio tones, displaying one or more light sequences, displaying one or more icons, displaying a written message, sending an e-mail notification, sending a text message notification, sending a small message service ("SMS") notification, sending a multi-media messaging service ("MMS") notification, or sending a chat message notification.

19. The method of claim 1, further comprising, receiving second user input, wherein measuring the second weight of the bag comprises measuring the second weight of the bag in response to the second user input.

20. The method of claim 1, wherein the location detection device is a global positioning system receiver, wherein the method further comprises determining the first location and the second location via the global positioning system receiver.

21. The method of claim 1, further comprising determining of the present location of the bag periodically.

22. An apparatus, comprising:
at least one processor;
a weight measurement device;
a user interface device;
a location detection device;
a computer readable storage medium in communication with the at least one processor, the computer readable storage medium having stored thereon computer software, the computer software comprising a set of instructions that, when executed by the at least one processor, causes the apparatus to perform one or more operations, the set of instructions comprising:
instructions to receive a first user input from a user to lock-in a first weight of a bag;
instructions to measure the first weight of the bag, in response to receiving the first user input;
instructions to store the measured first weight of the bag in the computer readable storage medium, prior to the user removing one or more items from the bag;
instructions to determine, with the location detection device, a first location of the bag when measuring the first weight of the bag;
instructions to store the first location in the computer readable storage medium:
instructions to determine that the bag is being moved by determining, with the location detection device, that a present location of the bag is different from the first location of the bag;
instructions to, based on a determination by the location detection device that the bag is being moved, measure a second weight of the bag and determine whether the second weight of the bag matches the stored first weight of the bag; and
instructions to, based on a determination that the second weight does not match the first weight, notify the user.

23. The apparatus of claim 22, further comprising:
a network interface device.

24. The apparatus of claim 22, wherein the user interface device comprises one or more of one or more display devices, one or more audio speakers, one or more touch-screen display devices, one or more buttons, one or more switches, or one or more light emitting devices.

25. The apparatus of claim 22, wherein the location detection device is a global positioning system receiver.

26. The apparatus of claim 22, wherein the set of instructions further comprises instructions to determine the present location of the bag periodically.

* * * * *